(12) United States Patent
Martinez et al.

(10) Patent No.: US 9,588,028 B2
(45) Date of Patent: Mar. 7, 2017

(54) MACHINE FOR TESTING CUSHIONING MATERIAL FOR PACKAGING

(75) Inventors: Manuel-Alfredo Garcia-Romeu Martinez, Valencia (ES); Juan Alcaraz Llorca, Valencia (ES); Amparo Martinez Giner, Valencia (ES); Enrique De La Cruz Navarro, Valencia (ES); Patricia Navarro Javierre, Valencia (ES); Javier Zabaleta Meri, Valencia (ES)

(73) Assignee: Instituto Technologico del Embalaje, Transporte y Logistica, Valencia (ES)

( * ) Notice: Subject to any disclaimer, the term of this patent is extended or adjusted under 35 U.S.C. 154(b) by 95 days.

(21) Appl. No.: 14/003,525

(22) PCT Filed: Mar. 8, 2012

(86) PCT No.: PCT/ES2012/070154
§ 371 (c)(1),
(2), (4) Date: Nov. 6, 2013

(87) PCT Pub. No.: WO2012/120179
PCT Pub. Date: Sep. 13, 2012

(65) Prior Publication Data
US 2014/0047898 A1    Feb. 20, 2014

(30) Foreign Application Priority Data
Mar. 8, 2011 (ES) .................. 201130309

(51) Int. Cl.
*G01M 7/00* (2006.01)
*G01N 3/00* (2006.01)
(Continued)

(52) U.S. Cl.
CPC ............ *G01N 3/303* (2013.01); *G01N 33/36* (2013.01); *G01N 2203/0033* (2013.01)

(58) Field of Classification Search
CPC ...................................................... G01N 3/303
(Continued)

(56) References Cited

U.S. PATENT DOCUMENTS 1,901,460 A * 3/1933 Lewis ......................... 73/12.13
2,846,869 A * 8/1958 Tyler et al. .................. 73/12.06
(Continued)

OTHER PUBLICATIONS

2010, H.H. Schueneman et al. "Package drop testing: the do's and don'ts of package impact performance tests". WETSPAK, Inc. revised Feb. 3, 2010.
(Continued)

*Primary Examiner* — Lisa Caputo
*Assistant Examiner* — Roger Hernandez-Prewit

(57) ABSTRACT

The invention relates to a machine for testing cushioning material for packaging, which improves the test method and performs a more precise characterization of cushioning for packaging. The machine is formed by: a load arm (1); a lift motor (2) on the upper part thereof; several guides that connect (i) a rigid platform (6) for positioning the sample to be tested, replaceable by a load cell (6'), and (ii) an impact platform comprising sensors (7) for monitoring the position thereof and measuring acceleration during impact; a spindle (4) for moving the load arm; and, on the lower part thereof, a seismic mass (5) for reducing the transmission of the impact.

8 Claims, 5 Drawing Sheets

(51) Int. Cl.
*G01N 33/00* (2006.01)
*G01P 15/00* (2006.01)
*G01N 3/303* (2006.01)
*G01N 33/36* (2006.01)

(58) Field of Classification Search
USPC .............................................. 73/12.01, 12.06
See application file for complete search history.

(56) References Cited

U.S. PATENT DOCUMENTS

| | | | |
|---|---|---|---|
| 3,103,116 A * | 9/1963 | Kohli | 73/12.06 |
| 3,402,593 A * | 9/1968 | Bresk et al. | 73/12.07 |
| 2004/0035181 A1* | 2/2004 | DeRuiter et al. | 73/12.06 |
| 2004/0261493 A1 | 12/2004 | Lee | |
| 2009/0297316 A1* | 12/2009 | Wells et al. | 414/737 |
| 2010/0039103 A1* | 2/2010 | Lenz et al. | 324/207.24 |

OTHER PUBLICATIONS

2001, M Sek and J Kirkpatrick "Corrugated cushion design handbook". ISBN 1-86272-598-5. 2001.
2000, M Sek et al. "A new method for the determination of cushion curves". Packaging technology and science 2000. 13: 249-255.

\* cited by examiner

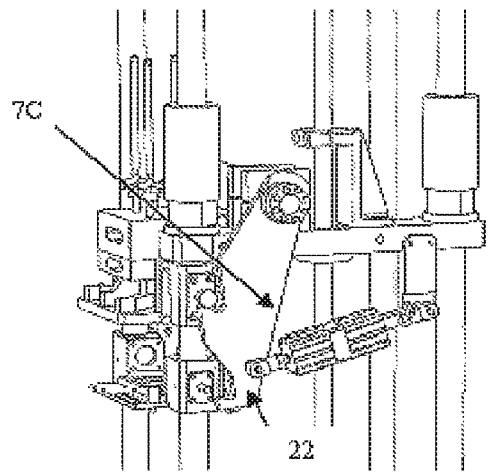 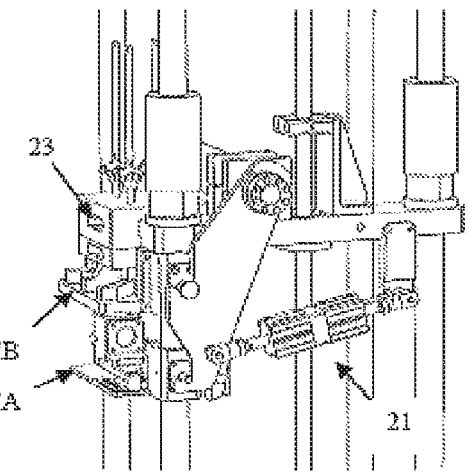
FIG.5A  FIG.5B
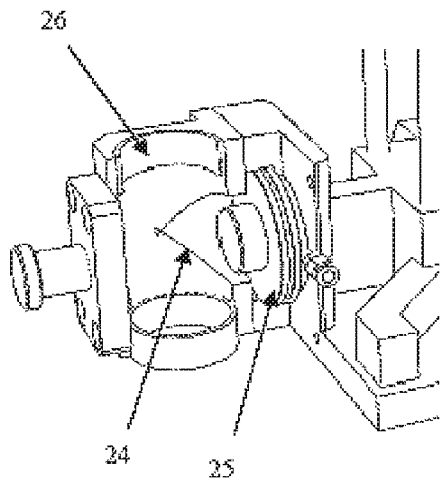 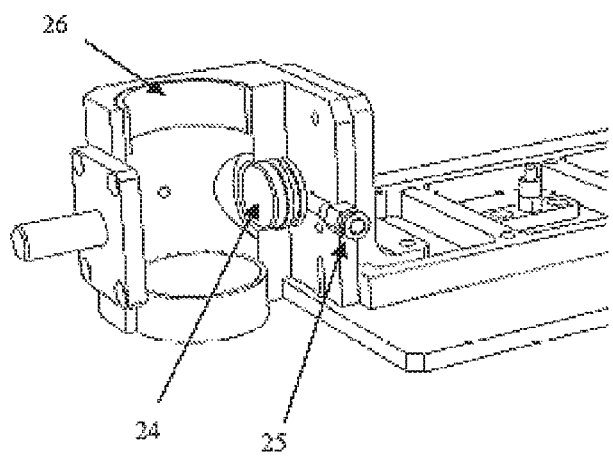
FIG.6A  FIG.6B

MACHINE FOR TESTING CUSHIONING MATERIAL FOR PACKAGING

The main object of the invention herein is a machine for testing cushioning material for packaging, which automates the process of loading and positioning the platform, and comprises at least one load cell that measures the force transferred during impact and a sensor for measuring the position of the platform at all times, in order to improve the test method, and provide a more precise assessment of the cushioning for packaging.

BACKGROUND OF THE INVENTION

The method for obtaining the cushioning curves of the packaging materials used to protect products consists of dropping a flat platform with a known mass onto the cushion sample to be tested from a specified height. The peak acceleration value produced during the test is measured by an accelerometer at the top of the platform. By repeating the test with different masses and from different heights, the characteristic curves of the cushioning material tested are obtained.

Current testing machines consist of a guiding plate comprising an anchoring system to raise or lower the load in order to position it at the desired drop height, having a system that releases the platform and an accelerometer that measures the acceleration peak. In addition, a brake actuator is provided that prevents the platform from hitting the cushioning material a second time, once it has rebounded. The drawbacks of such machines include the following:

(a) Although both lightweight and heavyweight platforms can be used to reach lower static loads during testing, the heavyweight platform must be removed to mount the lightweight platform, which is time-consuming.

(b) When using the lightweight platform, the braking and release mechanism is not actuated, and the entire operation has to be performed manually, with the resulting loss of precision in defining the drop height and possibly impacting a second time without being able to stop it by hand.

(c) When using one platform or the other, the drop height is established by using a millimeter ruler. As it is not controlled by a PLC (Programmable Logic Controller), but rather it is the operator who halts the platform at a particular height using the millimeter ruler, the low precision, combined with human error mean the tests are not very reproducible.

An example of this is the U.S. Patent US20090031783, which describes a resistance test apparatus for packages or other objects that consists of dropping or launching said object vertically downwards and verifying the damage produced. During launching various data are acquired, such as, for example, speed and acceleration.

Another apparatus that is also known is marketed by the company Lansmont in which a package is dropped, wherein the damage is determined. The structure of this apparatus consists of a plate that can slide vertically along a guide. However, in this case the package is arranged at a specified height above the plate, making the plate subsequently lower at a downward acceleration greater than gravity, such that the package drops in a free-fall state.

DESCRIPTION OF THE INVENTION

The test machine of the present invention solves the main drawbacks described above, in addition to automating the process of loading and positioning the platform, comprising a load cell that measures the force transmitted during impact and a sensor for measuring the position of the platform at all times, in order to improve the test method, and provide a more precise assessment of the cushioning for packaging. In turn, it is not necessary to remove the heavyweight platform in order to install the lightweight platform. Another novelty is that the lightweight platform also provides an automatic release and braking mechanism to prevent a second impact on the test sample.

The test machine that has been developed comprises a centralised electronic control system such that the user can know the position of the platform during the test with a precision of 0.025 cm (by using an encoder), can define the test height, position the platform with great precision and repeat the process as often as required. In this manner, the mechanical testing parameters are controlled and the number of test repetitions is further controlled. The machine includes a second encoder with a precision that can be read to 0.01 cm that continuously provides the position of the platform from the time the impact platform hits the cushioning material to be tested, resulting in greater measurement precision.

Said machine includes an accelerometer to know how the samples respond to the impact transmitted by the drop platform and to conduct tests in accordance with the conventional ASTMD1956 standard. This response is monitored by a digital acquisition system with adjustable sampling frequency that can be regulated between 1 kHz and 51.7 kHz.

One of its main novelties is that said machine can measure the position of the drop platform throughout the test, in time periods of up to 19.5 microseconds, and can further measure the force transmitted through the cushioning. With the new set of sensors that has been provided, the platform position, acceleration experienced and force it transmits can be simultaneously known.

As the rigid impact base where the sample to be tested is placed can be exchanged, by a load cell, and as an articulated compression arm that is placed on the test sample has been designed, the assembly can conduct a compression test at a constant speed to obtain the force-deformation curve.

Once this curve has been obtained, the articulated arm is removed and the path is left clear to conduct several impacts from different heights and/or different static loads to obtain cushioning curves applying the method developed by Michael Sek. A machine capable of obtaining cushioning curves by applying the conventional ASTMD1596 method and the Michael Sek method is obtained using this articulated device (Sek et al., 2000 Michael A. Sek, Merv Minett, Vincent and Ben Bruscella Rouillard, 2000. A new method for the determination of cushion curves. Packag. Technol. Sci. 2000, 13: 249-255.).

Using the conventional ASTM D1596 method, at least ten impacts are required in order to obtain the cushioning curve for a particular material, each one varying the calibrated masses on the impact platform, for each height and thickness of the material the cushioning curve is to be obtained for.

Using the Michael Sek method, in order to obtain a cushioning curve for a particular material, the force-deformation curve of the material has to be obtained by means of a compression test at constant speed and at least two impacts are required, each one varying the calibrated masses or the height of the impact platform for each material thickness the cushioning curve is to be obtained for. For example, using the Michael Sek method would require a tenth of the time than the conventional method in order to obtain the cushioning curves of a material with a given thickness for seven drop heights:

1) Conventional ASTM D1596 method:
   a) Ten impacts for each height (the calibrated masses of the impact platform must be changed ten times, and the heavyweight platform must be changed for the lightweight platform for at least two points of those ten impacts).
   b) TOTAL: seventy impacts, ten changes of calibrated mass, seven height changes for the drop platform and one change of the lightweight platform.
   c) Assuming that each change of the calibrated masses takes two minutes, that each height change takes one minute, that each change of platform takes ten minutes, that each impact takes one minute, then it will take 107 minutes to obtain the data necessary to draw the cushioning curves for that material for the seven drop heights.
2) Michael Sek method:
   a) One compression test at constant speed to obtain the force-deformation curve of the material.
   b) Two impacts, each one varying the calibrated masses or the height of the impact platform.
   c) TOTAL: Two impacts, one change of calibrated mass, one height change for the drop platform and zero changes of the lightweight platform.
   d) Assuming that each change of calibrated masses takes two minutes, that each height change takes one minute, that each change of platform takes ten minutes, that each impact takes one minute, that each compression test at constant speed takes five minutes, then it will take 10 minutes to obtain the data necessary to draw the cushioning curves for that material for the seven drop heights.

Another parameter that could not be calculated to date was the coefficient of restitution, and now, by having the height defined at all times with the encoder, the initial position, and the maximum height the plate reaches after impact with the sample, which are the values required for this calculation, can be known.

The entire device is assisted by a computer programme that keeps test records and processes real-time data, establishing not only the maximum acceleration transmitted but also provides the coefficient of restitution. Furthermore, the programme also controls the test parameters, giving the theoretical speed of the test, the actual speed of the test, the error thereof during the test and displays a warning if the error exceeds a predetermined value.

BRIEF DESCRIPTION OF THE FIGURES

Described very briefly hereinafter are a series of drawings that help to better understand the invention and which are expressly related to an embodiment of said invention that is presented as a non-limiting example thereof.

FIG. 1. shows a full view of the machine for testing cushioning material for packaging, which is the object of the present invention, wherein

FIG. 2. shows a detailed view of the support platform of the sample that forms part of the machine of the present invention, wherein

FIG. 5. shows a detailed view of the release mechanism of the impact platforms that forms part of the machine of the present invention, wherein FIG. 5A shows a first view of the mechanism in a release position and FIG. 5B shows a second view of the mechanism in a retracted position.

FIG. 6. shows a detailed view of the braking and sliding mechanism that forms part of the machine of the present invention, at two different cross sections (FIG. 6a and FIG. 6b).

PREFERRED EMBODIMENT OF THE INVENTION

Figures 1A, 1B:
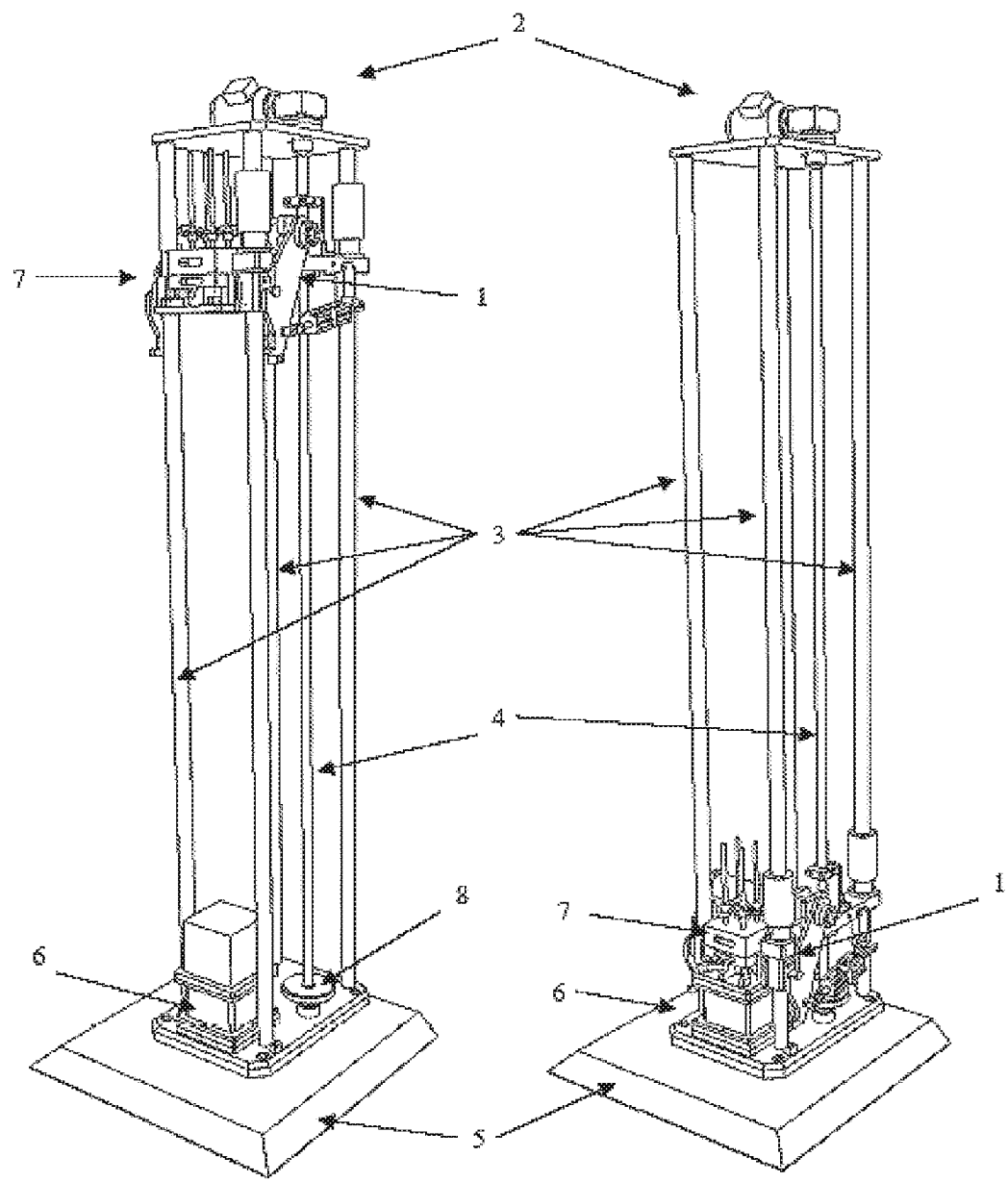
FIG. 1A shows the impact platform in an elevated position and FIG. 1B shows the aforementioned impact platform in a lowered position.
Figure 7A:
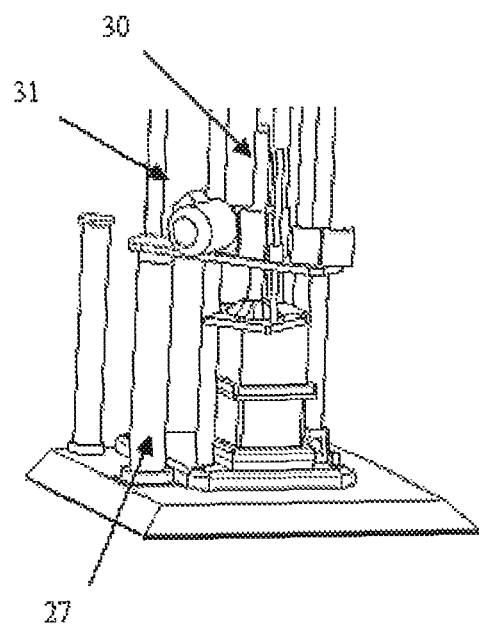
FIG. 7. shows a detailed view of the articulated arm for the compression test of the sample in two different positions (FIG. 7a and FIG. 7b)
Figure 7B:
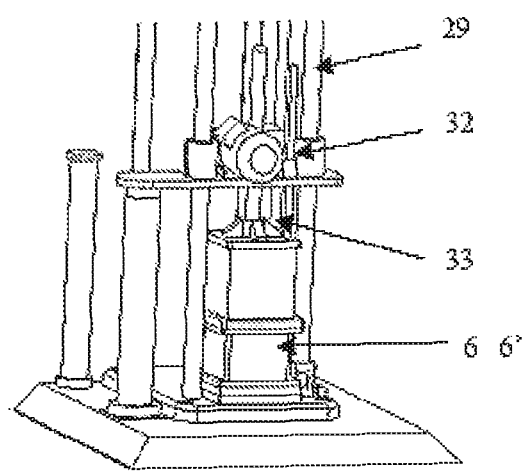

As shown by the accompanying figures, FIG. 1 shows a machine for testing cushioning material for packaging, not including the articulated arm shown in detail in FIG. 7, characterised in that it is formed by a loading arm (1), a lifting motor (2) at the upper part thereof, on a platform provided for that purpose, in addition to a plurality of guides (3) joining a support platform of the sample (6) and an impact platform (7) consisting essentially of a lightweight impact platform, the heavyweight platform and a release mechanism, wherein said impact platform (7) comprises a plurality of sensors for monitoring and measuring the position thereof and measuring the acceleration transmitted during the impact. The spindle (4) is configured for moving the loading arm (1), while a seismic mass (5) on the lower part thereof reduces the transmission of the impact.

Finally, the machine is completed by a flywheel (8) configured to establish a more precise reference for the drop height.

Figures 2A, 2B:
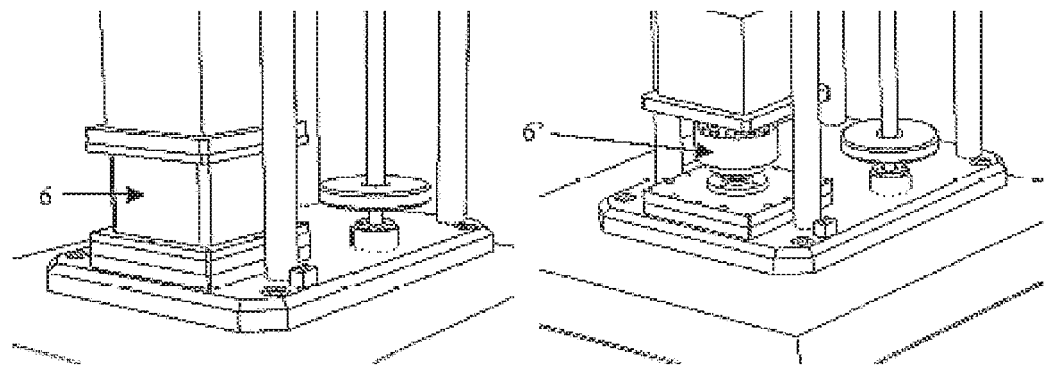
FIG. 2A shows the support platform for conventional tests and FIG. 2B shows the support platform for Sek-type tests.

FIG. 2 shows a detailed view of the support platform of the sample (6), that is formed by a rigid platform for positioning the sample to be tested, configured to conduct the cushioning materials assessment test using the conventional method; or interchangeable load cells (6'), 50 kN and 100 kN, configured for positioning the sample to be tested and for measuring the force produced during the test and to conduct the cushioning materials assessment test using the method developed by Michael Sek.

Figure 3:
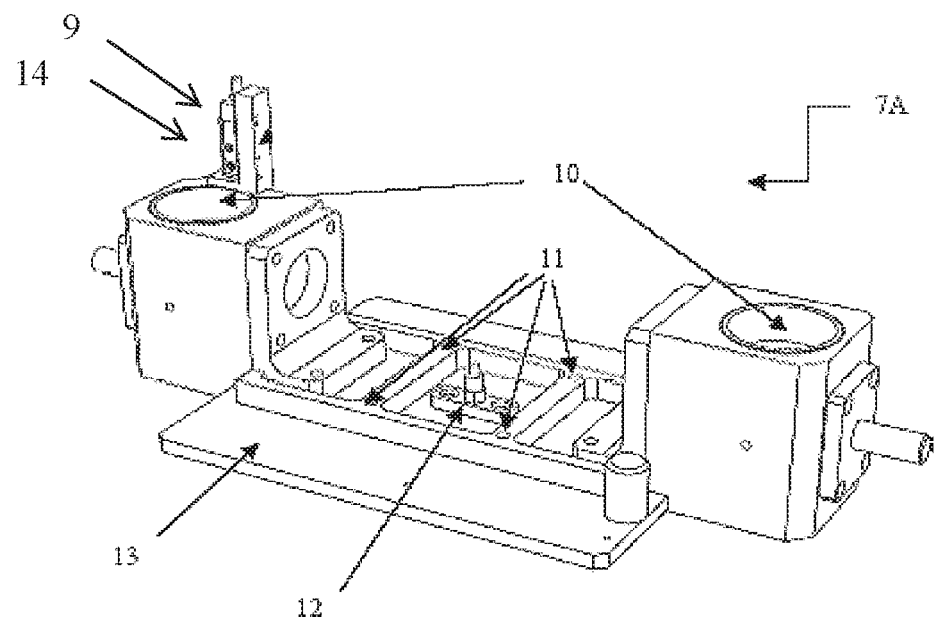
FIG. 3. shows a detailed view of the lightweight impact platform that forms part of the machine of the present invention.
Figure 4:
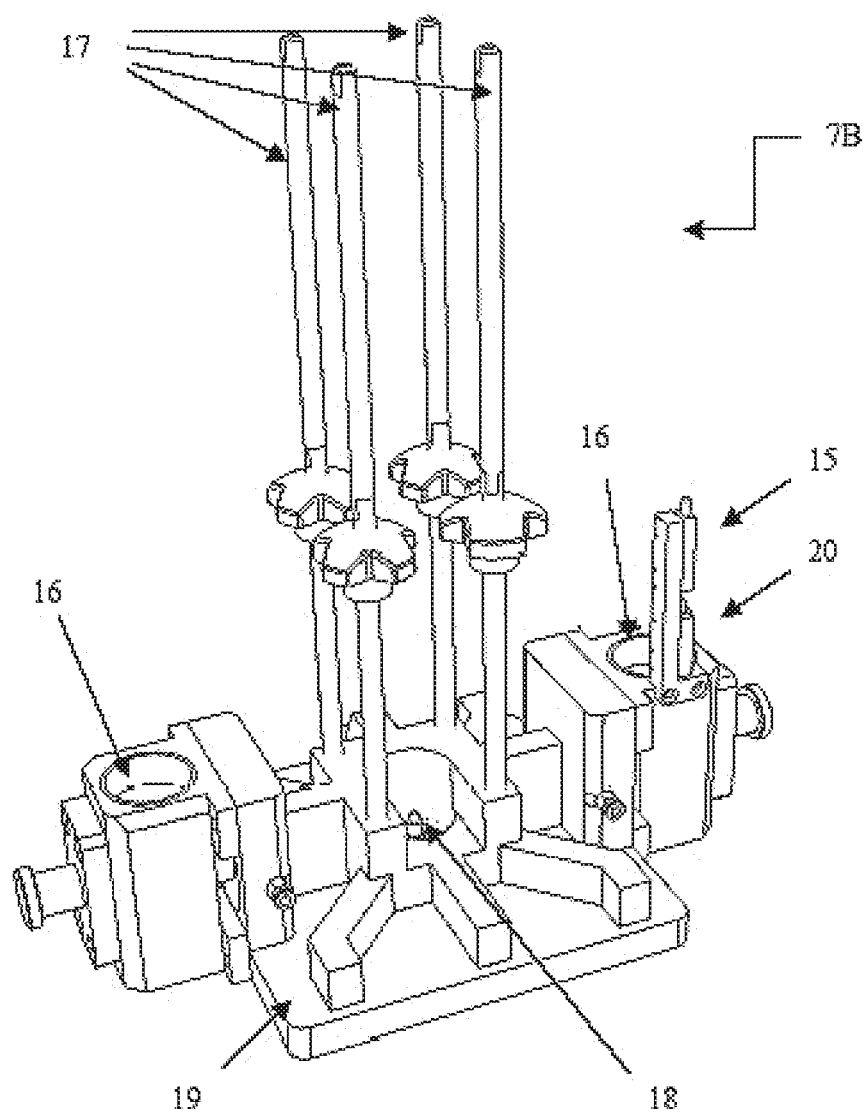
FIG. 4. shows a detailed view of the heavyweight impact platform that forms part of the machine of the present invention.

The impact platform (7) is shown in FIGS. 3, 4 and 5, showing the lightweight platform (7A) (FIG. 3) and the heavyweight platform (7B) (FIG. 4) in detail, that comprise the assembly, as well as the release mechanism for said platforms (7C) (FIG. 5).

Thus, the lightweight impact platform (7A) comprises at least one magnetic sensor (9) for measuring the position of the platform and for establishing the precise impact height of 0.025 cm, a plurality of low-friction bushings (10) for guiding the impact platform during freefall, a plurality of threaded holes (11) for inserting positioning rods for the calibrated weights required to reach the desired static load in each test, an accelerometer (12) for measuring acceleration during the impact and a lightweight impact platform (13) for reaching the low static loads and a second sensor (14) for measuring the position of the platform with greater precision, 0.001 cm., when the test is being conducted, once the impact platform is released.

On the other hand, FIG. 4 shows the heavyweight impact platform (7B) formed by a magnetic sensor (15) for measuring the position of the platform and to establish the precise impact height of 0.025 cm; a plurality of low-friction bushings (16) for guiding the impact platform during freefall; several threaded rods (17) for positioning the calibrated weights required to reach desired the static load in each test; an accelerometer (18) for measuring acceleration during the impact; a heavyweight impact platform (19); and a second sensor (20) for measuring the position of the platform with greater precision, 0.001 cm., when the test is being conducted, once the impact platform is released.

Finally, the impact platform (7) is completed with the release mechanism (7C) thereof, which, as shown in FIG. 5, is formed by a pneumatic actuator (21) for releasing the lightweight impact platform 7A and the heavyweight platform 7B, one release piece (22) common to both impact platforms, such that when the heavyweight impact platform is in place (7B), only the lightweight platform can be released and a plurality of calibrated weights (23) that can be placed on both the lightweight (7A) or the heavyweight platform. By way of completing the assembly, FIG. 6 shows the braking and sliding mechanism of the impact platform (7) in detail characterised in that it is formed by a pressure plate (24) whose braking operation is generated by an increase in pneumatic pressure supplied through the inlet orifice (25) and a plurality of low-friction bushings (26) such that the drop of the platform (7) resembles a free fall.

The release movement is generated by the pneumatic vacuum generated by a number of vacuum valves through the same inlet or outlet orifice (25), that generates the braking force and the release vacuum of the platforms.

FIG. 7 shows the articulated arm for the compression test of the sample, characterised in that the articulated arm (27) is manually operated to bring the compression unit to the test position, the fixed support arm (28) to rest the articulated arm when the compression unit is not in use, a bar (29) to prevent the support platform of the sample from rotating (6), that exerts pressure on the test sample, when the connector element (30) is actuated by the motor (31).

The connector element (30) moves up or down as it is actuated by the motor (31) to exert force on the sample to be tested.

The assembly is completed with a guide bushing (32) of the anti-rotation bar (29) comprising a position sensor that measures the displacement of the platform (33) during the compression test, and interchangeable 50 and 100 kN load cells (6'), for positioning the sample to be tested, to measure the force produced during the test and to conduct the cushioning materials assessment test using the method developed by Michael Sek.

The invention claimed is:

1. Machine for testing cushioning material for packaging wherein said machine configured to be displaced by a spindle, comprising:
   a lifting motor at an upper part of a machine;
   a plurality of guides extended between said lifting motor and a support platform located on a seismic mass;
   a lightweight impact platform and a heavyweight impact platform each slideably movable on said plurality of guides;
   a loading arm mechanically connected to a spindle extended between said lifting motor and said support platform and adapted to load said lightweight impact platform and said heavyweight impact platform;
   a release mechanism adapted to actuate said loading arm for releasing said lightweight impact platform while said heavyweight impact platform remains loaded on said loading arm and to move said loading arm for releasing said heavyweight impact platform when said lightweight impact platform is not in place;
   a plurality of sensors for monitoring a position of said lightweight impact platform and said heavyweight impact platform and for measuring an acceleration of said lightweight impact platform and said heavyweight impact platform during impact;
   wherein each of said plurality of sensors is attached to at least one of said lightweight impact platform and said heavyweight impact platform; and
   wherein said seismic mass is configured for reducing a transmission of the impact.

2. Machine for testing cushioning material for packaging according to claim 1, wherein the platform for the sample support comprises a number of interchangeable load cells, configured for positioning the sample and for measuring a force produced during a test.

3. Machine for testing the cushioning material for packaging according to claim 1 wherein each of said lightweight impact platform and said heavyweight impact platform has a braking and sliding mechanism.

4. Machine according to claim 3 wherein the lightweight impact platform comprises a first magnetic sensor for measuring a position of said lightweight impact platform during a freefall of said lightweight impact platform and for establishing an impact height; a plurality of low-friction bushings for guiding the lightweight impact platform during freefall; a plurality of threaded holes for inserting positioning rods of at least one calibrated weight required to reach a desired static load in each test; an accelerometer for measuring acceleration during the impact; a specific lightweight platform and a second magnetic positioning sensor for measuring said position of said lightweight impact platform during said freefall of said lightweight impact platform with higher measuring precision than said first magnetic sensor.

5. Machine for testing cushioning material for packaging according to claim 3, wherein the heavyweight impact platform comprises a first magnetic sensor for measuring a position of said heavyweight impact platform during a freefall of said heavyweight impact platform and for establishing an impact height; a plurality of low-friction bushings for guiding the heavyweight impact platform during freefall; several threaded rods for positioning at least one calibrated weight required to reach a desired static load in each test; an accelerometer for measuring acceleration during the impact; a specific heavyweight platform and a second magnetic positioning sensor for measuring said position of said heavyweight impact platform during said freefall of said heavyweight impact platform with higher measuring precision than said first magnetic sensor.

6. Machine for testing cushioning material for packaging according to claim 3 wherein said braking and sliding mechanism of each of said lightweight impact platform and said heavyweight impact platform comprises a pressure plate whose braking operation is generated by an increase in pneumatic pressure supplied through an inlet orifice; and a plurality of low-friction bushings such that a drop of the platforms resembles a freefall state; and wherein a release movement is generated by a pneumatic vacuum generated by vacuum valves through said inlet orifice or an outlet orifice, that generates a braking force and a release vacuum of the platforms.

7. Machine for testing cushioning material for packaging according to claim 1 wherein said release mechanism comprises a pneumatic, electric or hydraulic actuator to release the lightweight and heavyweight impact platforms, one release part common to the two lightweight and heavyweight impact platforms, such that when the heavyweight impact platform is in place, only the lightweight platform can be released; and a number of calibrated weights that can be put on both the lightweight or heavyweight platform.

8. Machine for testing cushioning material for packaging according to claim 1 wherein said loading arm comprises a release piece having two recesses, wherein a first of said two recesses is adapted for engaging said lightweight impact platform and wherein a second of said two recesses is adapted for engaging said heavyweight impact platform.

* * * * *

UNITED STATES PATENT AND TRADEMARK OFFICE
CERTIFICATE OF CORRECTION

| | |
|---|---|
| PATENT NO. | : 9,588,028 B2 |
| APPLICATION NO. | : 14/003525 |
| DATED | : March 7, 2017 |
| INVENTOR(S) | : Martinez et al. |

It is certified that error appears in the above-identified patent and that said Letters Patent is hereby corrected as shown below:

On the Title Page

Item (73) Assignee, Line 1:

"Technologico" should be changed to --Tecnologico--

Item (30) Foreign Application Priority Data:

"201130309" should be changed to --P201130309--

Signed and Sealed this
Twentieth Day of June, 2017

Joseph Matal
*Performing the Functions and Duties of the*
*Under Secretary of Commerce for Intellectual Property and*
*Director of the United States Patent and Trademark Office*